United States Patent [19]

Lambert et al.

[11] 4,312,806

[45] Jan. 26, 1982

[54] METHOD AND COMPOUNDS FOR TREATING INFLAMMATORY BOWEL DISEASE

[75] Inventors: Howard J. Lambert, Deerfield; Barnett S. Pitzele, Skokie, both of Ill.

[73] Assignee: G. D. Searle & Co., Skokie, Ill.

[21] Appl. No.: 239,813

[22] Filed: Mar. 2, 1981

[51] Int. Cl.³ .................. C07C 107/06; A61K 31/655; C09B 45/14
[52] U.S. Cl. .................................... 260/149; 260/207; 424/226; 424/154
[58] Field of Search ................................ 260/207, 149

[56] References Cited

U.S. PATENT DOCUMENTS

| | | | |
|---|---|---|---|
| 1,157,169 | 10/1915 | Mettler | 260/207 |
| 2,894,984 | 7/1959 | Hauptschein | 562/453 |
| 3,413,225 | 11/1968 | Dmuchovsky et al. | 260/207 |
| 3,674,844 | 7/1972 | Shen et al. | 562/453 |

OTHER PUBLICATIONS

King, Chemical Absts., 25, 1684(5), 1931.
Farbenind, Chemical Absts., 28, 5680(2), 1934.

*Primary Examiner*—G. T. Breitenstein
*Attorney, Agent, or Firm*—James G. Passé; Albert Tockman

[57] ABSTRACT

The present invention relates to novel compounds and a method for the prophylaxis and treatment of Inflammatory Bowel Disease (IBD) via the administration of an effective amount in a suitable pharmaceutical dosage form of an azobenzene compound of formula I or a pharmacologically acceptable salt, which is reductively cleaved to 5-aminosalicylic acid (5-ASA) by bacteria in the large intestine.

5 Claims, No Drawings

METHOD AND COMPOUNDS FOR TREATING INFLAMMATORY BOWEL DISEASE

BACKGROUND OF THE INVENTION

The present invention provides novel compounds and a novel method for the treatment of Inflammatory Bowel Disease (IBD) with certain azobenzene compounds. In particular it provides 5,5'-azobis-salicylic acid, a compound of formula I of Chart A, and its pharmacologically acceptable salts, which are reductively cleaved to 5-amino salicylic acid by the action of bacteria in the large intestine, and a method of treating or preventing IBD using said compounds.

In addition, it provides novel compounds of formula V of Chart A, the divalent alkali earth metal salts of 5,5'-azobis-salicylic acid. In addition, it further provides the novel trivalent aluminum salt of 5,5'-azobis-salicylic acid, formula VI of Chart A.

IBD is a chronic, nonspecific, inflammatory and ulcerative disease of the colon, and may be characterized by bloody diarrhea. An example is ulcerative colitis. In ulcerative colitis the disease begins in the rectosigmoid area and may extend proximally, eventually involving the entire colon, or it may involve the large bowel at once. See Cecil, Textbook of Medicine, 1568–1578.

Treatment of IBD has been accomplished by several pharmacological routes. Notably, adrenocorticosteroids, belladonna alkaloids, belladonna derivatives, bismuth subcarbonate, kaolin and sulfasalzine are in current use. The adrenocorticosteroids may mask symptoms of intestine perforation and peritonitis and are generally only used for short term therapy, (Goodman & Gilman 4th Ed. pg. 1634 (1970)) and Major complications may occur despite corticosteroid therapy. The belladonna alkaloids and derivatives are largely considered ineffective in IBD. (Goodman & Gilman 4th Ed. pg. 544 (1970). Bismuth subcarbonate is a mechanical protectant and merely prevents further irritation of the condition without any direct effect on the condition. Kaolin is an absorbent which absorbs bacteria and toxins in the colon, but it is doubtful that appreciable activity is retained by the time it reaches the lower bowel. (Goodman and Gilman 4th ed. pg. 990 (1970). Sulfasalazine (SS) is the drug of choice currently for IBD. Its structure is shown in formula II of Chart A. SS is a pro-drug, that is, upon administration, biological processes act upon SS to produce the drug which has the desired biological activity. Upon oral administration, about one-third of a given dose of SS is absorbed from the small intestine. The remaining two-thirds are split by azo-reductase from bacterial flora into sulphapyridine (SP), formula III of Chart A, and 5-aminosalicylic acid (5-ASA) formula IV of Chart A. (Physcan's Desk Reference 31st ed. pg. 1250 (1977) See also Klotz, New Eng J. of Med 303, 1499 (1980). It has been determined that the activity of SS comes from the 5-ASA produced. SS is effective as a pro-drug because its relative insolubility prevents its complete absorption in the small intestine thus allowing delivery of SS to the site of administration, i.e., the large intestine. Given separately, both SP and 5-ASA are almost completely absorbed from the small intestine. While effective, SS has several severe side effects including blood dyscrasias and hypersensitivety reactions. This toxicity of SS is due almost entirely to the SP produced.

PRIOR ART

The pharmacological treatment of IBD is well known as indicated above. SS is described in U.S. Pat. No. 2,396,145 (1946). 5,5'-azobis-salicyclic acid is described in Great Britain patent 408,676 (1934). The only use described is as a dyestuff. A number of articles have described the therapeutic effectiveness of 5-ASA and SS, its efficacy, as well as the toxicity problems of SS. Of note is Khan, et al, *The Lancet*, 292 Oct 29, (1977); Hees, et al, Gut 21, 632–635 (1980) and Klotz, et al, *N. Engl. J Med* 303 1499–1502 (1980).

SUMMARY OF THE INVENTION

The present invention particularly provides: a method of treatment or prevention of IBD in a mammal suffering from or susceptible to the development of IBD which comprises administering an amount of 5,5'-azobis-salicyclic acid or its pharmacologically acceptable salt effective to treat that condition. In addition it provides novel compounds of formula V, the alkali earth metal salts of 5,5'-azobis-salicyclic acid wherein $M^{++}$ represents the divalent alkali earth metals. In addition it provides the novel aluminum salt of 5,5'-azobis-salicyclic acid, formula VI of Chart A.

The compounds of the instant invention are useful in that they are readily reduced to 5-ASA in the colon by intestinal bacteria. 5-ASA is in fact the only product of the reduction. 5-ASA yields two moles of 5-ASA for every mole of a compound of the invention that is reduced. This reduction is accomplished without a potentially toxic sulfa compound being produced. Thus, a dose of the compounds of the instant invention maybe given, and a therapeutic amount of 5-ASA released. In addition, the novel alkali earth metal, and novel aluminum salts of 5,5'-azobis-salicyclic acid, because of their surprising solubility properties i.e., less soluble, are less readily absorbed in the small intestine than is 5,5'-azobis-salicyclic acid. This is desirable in that less compound needs to be given to obtain a final determined dose of 5-ASA, and a decrease in systemic undesirable side effects results.

The novel alkali earth metal salts are prepared from the free acid by refluxing the appropriate oxide or hydroxide e.g. calcium hydroxide, in water, then filtering, washing and drying.

The novel aluminum salt is prepared by refluxing 2 moles of aluminum hydroxide with 1 mole 5,5'-azobis-salicyclic acid for an appropriate time.

By virtue of the anti-IBD activity, 5,5'-azobis-salicyclic acid and the pharmacologically active salts are useful in treating IBD in humans and animals. A physician of ordinary skill could readily determine a subject who is exhibiting IBD symptoms. Regardless of the route of administration selected, the compounds of the present invention are formulated into pharmaceutically acceptable dosage forms by conventional methods known to the pharmaceutical art.

The compounds can be administrated in such oral unit dosage forms such as tablets, capsules, pills, powders, suspension or solution or granules. They also may be administered rectally, in such forms as suppositories, creams, ointments or enemas using forms known to the pharmaceutical art. In general, the preferred route of administration is oral.

An effective but non-toxic quantity of the compound is employed in treatment. The dosage regimen for prevention or treating IBD by the compounds of this invention is selected in accordance with a variety of factors including the type, age, weight, sex and medical condition of the mammal, the severity of the IBD and the route of administration. An ordinarily skilled physician or veterinarian could employ relatively low dosages at first, subsequently increasing the dose until a maximum response is obtained.

Initial dosages of the compounds of the invention are ordinarily in the area of 5 mg/kg up to at least 100 mg/kg orally.

The compounds of this invention can also be administered as pharmacologically acceptable mono or polyvalent cationic salts such as sodium, calcium, magnesium, strontium, aluminum, and the like. Alkali earth metal salts include calcium, magnesium and strontium. Additionally, the compounds of this invention may be administered in a suitable hydrated form.

DESCRIPTION OF THE PREFERRED EMBODIMENTS

The compounds of the present invention are useful in the treatment of IBD as shown by one or more of the following tests.

EXAMPLE 1

In Vitro

No animal model exists for testing the efficacy of therapeutic modalities for the treatment of IBD. The following test determines the reduction of azo bonds by colonic bacteria in order to release 5-ASA.

A. In Vitro Bacterial Incubation

1. Sample Preparation: Two pure bacterial cultures normally found in the colon were used: *Klebsiella pneumoniae* (ATCC4352)in trypticase soy broth; and *Bacteroides fragilis* (ATCC23745) in fluid thioglycollate medium. Compounds dissolved or suspended in DMSO were added to 5 ml of sterile media or to 5 ml of media which had been inoculated with bacteria 24 hours previously. Each time a compound was incubated, additional inoculates were incubated with 5-ASA and SS. Each 100 ml of DMSO contained the same molar equivalents of 5-ASA. Cultures and control media were incubated for 45-48 hours at 37° C.

2. Sample Analysis: Bacterial cultures and control media were filtered with a final filter size of 0.45 microns. The filtrates were applied directly to Merck GF-254 silica TLC plates (EM Laboratories, Darmstadt, Germany along with 5-ASA standards at various concentrations from 50 ng to 450 ng/5 $\mu$l. Additionally, standards of SS and each compound were also applied to the TLC plate. Plates were developed to 16 cm in saturated tanks of three types:

(a) Ethanol:NH$_4$OH (99:1, v/v)
(b) Butanol:Butanone:H$_2$O (40:40:20, v/v)
(c) Isopropanol:H$_2$O:NH$_4$OH (70:20:10, v/v)

Plates were examined within 10 minutes after development under longwave U.V. (365 nm) light and the intensity of the green fluorescence produced by 5-ASA (produced by azo-reduction of compounds of the invention) was compared to 5-ASA standards, 5-ASA incubated with bacteria, and SS incubated with bacteria.

In this test the amount of 5-ASA produced after incubation in contact with bacteria is a measure of the degree of azo-reduction of invention compound to 5-ASA by bacteria. Comparison of these compounds with the data derived from SS would reveal those compounds that release equivalent amounts of 5-ASA under identical conditions. Controls acted as a check to show that without bacteria, no azo-reduction took place, and that the compound or any breakdown products did not fluoresce green at the same R$_f$ as 5-ASA. Therefore, these data provided evidence that the reductive release of 5-ASA from 5,5'-azobis-salicyclic acid and its salt occurs.

TABLE 1

| Compound | Percent Formation of 5-ASA[1] | |
|---|---|---|
| | Bacteroides Culture | Klebsiella Culture |
| Sulfasalazine (SS) | 100 | 100 |
| 5,5'-azobis-salicyclic acid | 100 | 75 |
| 5,5'-azobis-salicyclic acid dicalcium salt | 100 | 100 |
| 5,5'-azobis-salicyclic acid, dimagnesium salt | 100 | 75 |

[1]Formation of 5-ASA is compared to that released by SS, which is defined as 100 percent.

EXAMPLE 2

In Vivo

The objective of this test is to determine if a compound as identified in Example 1 testing would produce an equivalent amount of 5-ASA, to that produced in the colon of rats after oral administration of SS.

Administration of Selected Compounds of Rats:

1. Animals: Female rats weighing 240-270 g were fasted overnight. One group of six rats was administered 125 mg SS orally while another group was given 62 mg of 5,5'-azobis-salicylic acid orally. These amounts were equimolar for 5-ASA such that total reduction of azo bonds in both compounds would release 47.5 mg 5-ASA in each rat in both groups. The compounds were suspended in a 0.5% methylcellulose, 0.1% Tween 80 mixture. Feces were collected from each rat at 24, 48 and 72 hours.

2. Sample Preparation and Analysis: The samples were analyzed twice. For the first analysis, fifty percent of each fecal sample from each treatment group was combined for all rats and time points. For the second analysis, feces from individual rats from each group were combined from 0-72 hours and each rat's feces was analyzed separately. A ten gram aliquot of feces from rats administered 5,5'-azobis-salicylic acid, dicalcium salt or SS was mixed with 10 ml of H$_2$O and extracted with 300 ml methanol in a soxhlet apparatus. The same amount of feces was spiked with varying amounts of 5-ASA and treated in a similar manner. In addition, SS, 5,5'-azobis-salicylic acid, dicalcium salt and 5-ASA were spiked into feces, allowed to sit at room temperature for 24 hours and then treated in the same manner as the samples. This was to mimic the amount of time the feces sat in the collecting apparatus.

The methanol extract of feces for all samples was adjusted to a constant volume. Two ml of each extract was blown to dryness and reconstituted in 100 $\mu$l of methanol. The same volume of each extract was spotted on TLC plates which were developed and read at the same time. The samples were visually compared to the control samples spiked with from 1 to 20 mg.

3. Results: The results of control feces spiked with 5-ASA over the range of 1 to 20 mg indicated that each of the levels could be discriminated from each other and that the intensity increased with increasing amounts of 5-ASA added to the feces. In addition, insignificant breakdown of 5-ASA, SS or 5,5'-azobis-salicylic acid, dicalcium salt was seen in control samples spiked with these compounds. In addition, the results from the fecal samples whether analyzed as a total combined pool or for individual rats were the same.

The amount of 5-ASA seen in feces from animals dosed with SS appeared to be the same as in the 3 mg level spiked control. This indicates that 6% of the theoretical amount of 5-ASA that could be produced from total cleavage of the dosed SS was eliminated in the feces. The amount of 5-ASA seen in feces from animals dosed with 5,5'-azobis-salicylic acid, dicalcium was more than that in the 3 mg level spiked control but less than the 7 mg control. This indicates that from 6% to 15% of theoretical 5-ASA was eliminated in feces from animals dosed with 5,5'-azobis-salicylic acid, dicalcium salt. This indicates that the release of 5-ASA from 5,5'-azobis-salicylic acid and its salts is qualitatively the same or better than that obtained from SS. As a literature reference for these experiments see, Eastwood, *Therap. Drug Monit.* 2:149–152, (1980); Peppercorn et al, *Gastroenterology* 64:240–245, (1973): Peppercorn et al, *J. Pharm. and Exper. Therap.* 181:555–562, (1972); Kirsner, JAMA 243:557–564, (1980); and the references listed in the prior art section.

EXAMPLE 3

5,5'-azobis-salicylic acid, dicalcium salt (formula V: M++ is calcium++).

5,5'-azobis-salicylic acid, 3.03 g. (9.75 mmole) is combined with CaO (19.5 mmole, taking care to get an analysis of the CaO to detect any Ca(OH)$_2$ formation, which will change the equivalent weight) in a 100 ml pear-shaped flask, with the addition of H$_2$O (35 ml). The suspension is agitated with a magnetic stirrer and refluxed for 16 hr. The mixture is allowed to cool slightly, and is filtered while still warm. The solid is washed with distilled water, and dried in a vacuum oven at 102° overnight (about 16 hr). The resulting solid is ground to a green-black powder, and analyzed (C,H,N,Ca) to give the desired product as the monohydrate $C_{14}H_6N_2O_6Ca_2.1\ H_2O$ mw 396.39. UV-Visible Spectral data: at pH 7–7.5 $\lambda_x=360$ nm, $\epsilon=2.2\times10^4$.

EXAMPLE 4

5,5'-azobis-salicylic acid dimagnesum salt (formula V: M++ is Magnesium++)

5,5'-azobis-salicylic acid, 5.0 g (16.55 mmole), is combined with MgO (33.09 mmole, taking care to get an analysis of the MgO to detect any Mg(OH)$_2$ formation, which will change the equivalent weight), light powder, in a 100 ml pear shaped flask containing a magnetic stirrer. Distilled water (60 ml) is added, and the resulting mixture is stirred and refluxed for 1.5 hr. The mixture is then filtered while still hot. The solid is washed with H$_2$O. The filtrate and washes are discarded, and the solid is resuspended in distilled H$_2$O (50 ml) and stirred at room temperature overnight. More distilled water (20 ml) is then added to the stirring mixture, which is then refluxed for 2 hr. The mixture is filtered while hot, and the solid is washed with distilled water. It is then dried overnight in a vacuum oven (102°) to give the desired product as the complex with Mg(OH)$_2$ and H$_2$O: $C_{14}H_6N_2O_6Mg_2.\tfrac{1}{2}Mg(OH)_2.2\tfrac{1}{2}H_2O$ mw 421.02 (C,H,N,Mg).

UV-visible spectral data: at pH 7–7.5 $\lambda_x=361$ nm $\epsilon=2.2\times10^4$.

EXAMPLE 5

5,5'-azobis-salicylic acid, distrontium salt (formula V:M++ is Strontium++).

5,5'-azobis-salicylic acid, 6.24 g (20.65 mmole) is combined with hydrated Sr(OH)$_2$ (41.3 mmole, taking care to get an analysis of the Sr content to ascertain extent of hydration, and thus, molecular weight) in a 500 ml round bottom flask, with the addition of distilled H$_2$O (200 ml) and a magnetic stirrer. The mixture is stirred and refluxed 16 hr. The mixture is the filtered while hot, and the solid is washed with distilled H$_2$O. The filtrate and washes are discarded, and the solid is resuspended in distilled H$_2$O (100 ml) and stirred at room temperature for 1.5 hr. The mixture is then heated to boil momentarily, and filtered while hot. The solid is washed with distilled H$_2$O, and then dried in a vacuum oven at 105° overnight. The resulting desired product occurs as a complex with Sr(OH)$_2$ and H$_2$O: $C_{14}H_6N_2O_6Sr_2.1/12Sr(OH)_2.1\tfrac{1}{2}H_2Omw$ 510.61 (C,H,N,Sr). UV-visible spectral data: $\lambda_x=360$ nm, $\epsilon=2.1\times10^4$.

CHART A

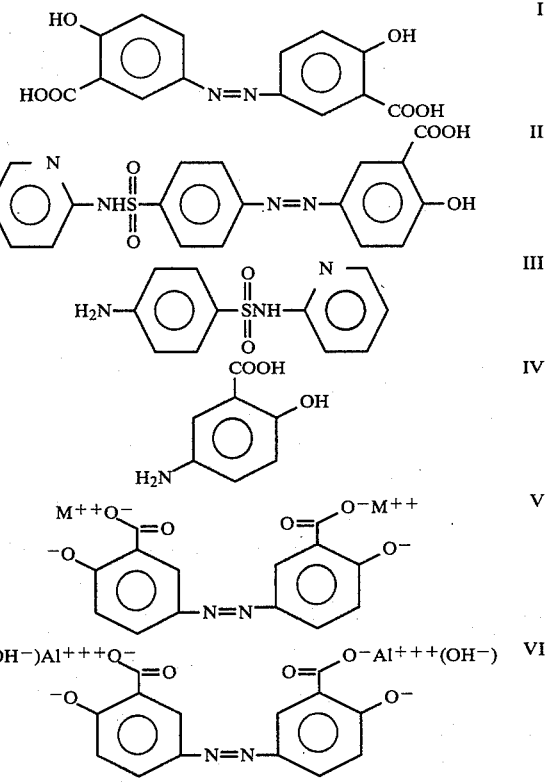

2. 5,5'-azobis-salicylic acid, dicalcium salt, a compound according to claim 1.
3. 5,5'-azobis-salicylic acid, dimagnesium salt, a compound according to claim 1.
4. 5,5'-azobis-salicylic acid, distrontium salt, a compound according to claim 1.
5. 5,5'-azobis-salicyclic acid, dialuminum salt, of the formula:
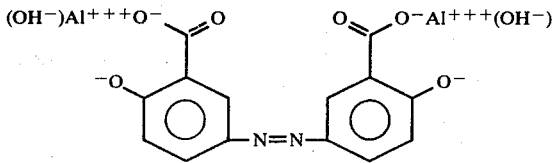

We Claim:
1. A compound of the formula:

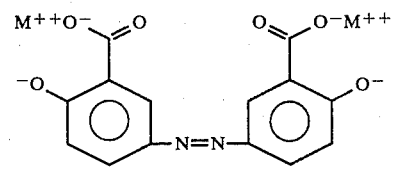

wherein M++ is a divalent alkali earth metal.